United States Patent
Sen Dogan et al.

(10) Patent No.: US 12,036,554 B2
(45) Date of Patent: Jul. 16, 2024

(54) MICROFLUIDIC DEVICE FOR SELECTIVE CAPTURE OF BIOLOGICAL ENTITIES

(71) Applicant: MIKRO BIYOSISTEMLER ELEKTRONIK SANAYI VE TICARET A.S., Ankara (TR)

(72) Inventors: Begum Sen Dogan, Ankara (TR); Ender Yildirim, Ankara (TR); Ozge Zorlu, Ankara (TR); Ebru Ozgur, Ankara (TR)

(73) Assignee: MIKRO BIYOSISTEMLER ELEKTRONIK SANAYI VE TICARET A.S., Ankara (TR)

( * ) Notice: Subject to any disclaimer, the term of this patent is extended or adjusted under 35 U.S.C. 154(b) by 616 days.

(21) Appl. No.: 17/418,868

(22) PCT Filed: Aug. 6, 2019

(86) PCT No.: PCT/TR2019/050649
§ 371 (c)(1),
(2) Date: Jun. 28, 2021

(87) PCT Pub. No.: WO2020/139229
PCT Pub. Date: Jul. 2, 2020

(65) Prior Publication Data
US 2022/0072552 A1    Mar. 10, 2022

(30) Foreign Application Priority Data
Dec. 28, 2018    (WO) ................ PCT/TR2018/050934

(51) Int. Cl.
*B01L 3/00*         (2006.01)
*G01N 33/543*    (2006.01)
*G01N 33/574*    (2006.01)

(52) U.S. Cl.
CPC .... *B01L 3/502761* (2013.01); *B01L 3/502746* (2013.01); *B01L 2200/0652* (2013.01); *B01L 2200/12* (2013.01); *B01L 2300/0848* (2013.01); *B01L 2300/0883* (2013.01); *B01L 2300/089* (2013.01); *G01N 33/54366* (2013.01); *G01N 33/574* (2013.01)

(58) Field of Classification Search
CPC ....... G01N 15/1484; G01N 2015/1006; G01N 33/54366; G01N 33/574; B01L 2200/0652; B01L 2200/12; B01L 2300/0848; B01L 2300/0883; B01L 2300/089; B01L 3/502746; B01L 3/502761
See application file for complete search history.

(56) References Cited

U.S. PATENT DOCUMENTS

2011/0301058 A1* 12/2011 Cheng ................ B01L 3/5027 506/9
2017/0248508 A1* 8/2017 Ward ................ G01N 33/5091

* cited by examiner

Primary Examiner — Jennifer Wecker
(74) Attorney, Agent, or Firm — Bayramoglu Law Offices LLC

(57) ABSTRACT

A microfluidic device is provided. The microfluidic device is used for an in vitro selective capture of biological entities suspended in a medium based on an immunoaffinity technique. The microfluidic device includes symmetric hydrofoil pillars arranged inside ellipse segments acting as a microfluidic channel, wherein the microfluidic channel provides a continuous change of attack angles between the symmetric hydrofoil pillars and the biological entities.

14 Claims, 9 Drawing Sheets

MICROFLUIDIC DEVICE FOR SELECTIVE CAPTURE OF BIOLOGICAL ENTITIES

CROSS REFERENCE TO THE RELATED APPLICATIONS

This application is the national stage entry of International Application No. PCT/TR2019/050649, filed on Aug. 6, 2019, which is based upon and claims priority to International Application No. PCT/TR2018/050934 filed on Dec. 28, 2018, the entire contents of which are incorporated herein by reference.

TECHNICAL FIELD

The present invention relates to microfluidic device for selective capture of biological entities suspended in a medium and to medical diagnostics.

BACKGROUND

Cancer is the second common cause of deaths worldwide (8.8 million deaths in 2015) associated with an important economic burden (up to 4% of global GDP).

The initial diagnosis of cancer requires invasive tissue biopsy of the tumor, an expensive, lengthy and painful process that carries significant risk of infection. Its greatest limitation is that sampling of a single tumor may not capture all the mutations present, since cancer evolves genetically over time, necessitating continuous monitoring for personalized therapy. A promising solution is the liquid biopsy, which involves sampling from bodily fluids, mainly blood, to analyze cancer biomarkers.

Circulating Tumor Cell (CTC) enrichment/isolation systems are one of the main pillars in liquid biopsy market and expected to reach $8.7B in 2020, with CAGR of 15% (Grand View Research, 2016).

CTCs are the cells that disseminate into blood from primary or metastatic tumors and play a crucial role in metastatic cascade. Prognostic value of CTCs has been proven and approved by FDA for breast, prostate and colorectal cancer, where the higher number CTCs (>5 CTCs/7.5 ml blood) is correlated with lower overall survival rate (OSR) as a result of CellSearch® study.

Other potential clinical utilities of CTCs include disease monitoring, therapy guidance, patient stratification for precision medicine and personalized therapy, screening for early diagnostics, cancer research, and drug development. The main challenge in the use of CTCs in routine clinical practice arises from the difficulty of their isolation from blood as they are extremely rare (as low as one CTC in a billion blood cells).

None of the current CTC isolation technologies can provide necessary sensitivity, reliability, robustness, ease of use and cost efficiency, which are the most important user needs in terms of clinical and economic perspectives.

There are currently around 40 companies in the competitive landscape for the CTC market. Among these, there is only one FDA-approved CTC detection system in the market, from the Janssen Diagnostic company (CellSearch®), recently acquired by Menarini Silicon Biosystems. The system is widely considered as the gold standard for the enumeration of CTCs of breast, prostate, and colorectal cancers. A single test costs around $450 to $600, in US and Europe. Although approved by FDA, CellSearch® is not in routine clinical use mostly due to its high cost of infrastructure and centralization in certain clinics causing sample transfer problems.

Besides, the technologies developed afterwards have reported much higher CTC numbers for the same clinical samples, decreasing the reliability of the system.

The CTC isolation platforms that utilize microfluidic technologies for immunoaffinity-based CTC isolation are IsoFlux (Fluxion Biosciences), LiquidBiopsy (Cynvenio), Biocept and Biofluidica.

The IsoFlux (Harb W., et al., 2013) and LiquidBiopsy (Winer-Jones J. P. et al., 2014) platforms utilize Ficoll-density centrifugation for pre-enrichment and off-chip immunomagnetic labelling of CTCs in the sample before loading the sample into microfluidic chip for magnetic separation under microfluidic flow. The main drawbacks of these technologies are the long pre-processing time for sample preparation to enrich CTCs before sample loading. The latter two systems, on the other hand, utilize antibody-coated microfluidic channels for isolation of CTCs from biological fluids, similar to the method and device proposed within the frame of this invention.

The technology presented in U.S. Pat. No. 9,250,242B2 is based on the antibody coated, parallel, narrow (25 µm) and deep sinusoidal microfluidic channels, which favors the rolling motion of the cells on the surfaces. In contrast, the proposed invention suggests a wider channel including pillars to alter the flow path of the biological entities.

The channel design presented in US 2006/0160243A1 is based on the antibody coated cylindrical pillars arranged randomly in a microfluidic channel. The cylindrical pillars have differing diameters. The device enhances the flow path of the biological entities so that straight-line flow is interrupted by a pattern of transverse posts. In a similar manner, US 2014/0154703A1 encompasses methods and microfluidic device for diagnosis of cancer comprising an input, an output and an array of obstacles disposed there-between and further comprising support pillars coated with antibody. Diameter of each of the support pillars and distance between pillars can change according to the different channel regions. US 2007/0026417A1 discloses a method for detecting, enriching, and analyzing circulating tumor cells and other particles. The shape of obstacles is cylindrical. Due to the antibody-antigen interaction on pillar, cells could be captured. In contrast to the cylindrical obstacles proposed in the mentioned previous inventions, the proposed invention herein provides a chaotic trajectory for the biological entities by symmetric hydrofoil shaped pillars arranged regularly inside a microfluidic channel formed by ellipse segments. All the pillars have the same dimensions and the invention increases collisions the between biological entities and the pillars by increasing the surface area and by scanning all the attack angles.

SUMMARY

In the present invention a microfluidic device, which provides selective capture of biological entities suspended in a medium is proposed.

The device enables a continuous change of the attack angle, thus keeping the chaotic trajectories of the biological entities throughout the channel.

The device includes pillars in droplet shape, resulting in increased entity/surface interaction probability to capture the target biological entities among various other entities in a suspension, which results in increase in the capture efficiency (sensitivity), which is defined as the percent ratio of the number of captured target biological entities in the capture volume to the total number of target biological entities entering the capture volume.

The increase in entity/surface interaction enables increasing the inter-pillar distances to a value of at least three to ten times of the target entity's characteristic dimension instead of the typical value of two to three times of the target entity's characteristic dimension, without compromising the capture efficiency. Wider pillar distance decreases the probability of channel clogging while the sample is passing through the channel. This is especially important when working with the high concentration suspensions.

In a particular embodiment for capturing CTCs from bodily fluids, such as blood, the increase in entity/surface interaction provides the use of 75-150 μm inter-pillar distances instead of 50-70 μm, without compromising the cell capture efficiency.

The pillars are in the same shape and distribution pattern throughout the channel that significantly reduce the design input parameters, resulting in a simplified design procedure.

Furthermore, wider inter-pillar distances provide versatility in the manufacturing processes including various polymer molding options.

The device maintains chaotic trajectories for the biological entities throughout the channel without changing the pillar shape and arrangement. This is realized by utilizing a meandering microfluidic channel and symmetric hydrofoil shaped pillars distributed as an array, wherein the geometric centers of the pillars in the array form a rhombic lattice.

The inventive step is to define fluid streamlines over a uniformly distributed pillar pattern by incorporating a channel structure as described above, leading to continuously changing attack angle throughout the channel. This brings about the following advantages:

Higher sensitivity: High efficiency capture of biological entities due to higher frequency of entity/surface interaction.

Clogging-free channel operation: The increase in entity/surface interaction provides increase in inter-pillar distances at least three to ten times of the target entity's characteristic dimension instead of the typical value of two to three times of the target entity's characteristic dimension, without compromising the capture efficiency. Wider pillar distance decreases the probability of channel clogging while the sample is passing through the channel. This is especially important when working with the high concentration suspensions.

Ease of design: Simplified design procedure with significantly reduced design input parameters due to the uniformly distributed pillar pattern.

Versatile and cost-effective device manufacturing: Wider inter-pillar distances provide versatility in the manufacturing processes including various polymer molding options.

The application of the invention will be on biomedical microsystems for in vitro diagnostic (IVD) or research use only (RUO) purposes. One application example is detection of biological entities, such as CTCs from the blood samples of cancer patients. CTCs in the blood sample can be selectively captured among other peripheral blood cells thanks to their distinct surface proteins, which selectively interacts with the coated antibody on the channel surface.

DESCRIPTION OF THE COMPONENTS AND PARTS OF THE INVENTION

Figure 1:
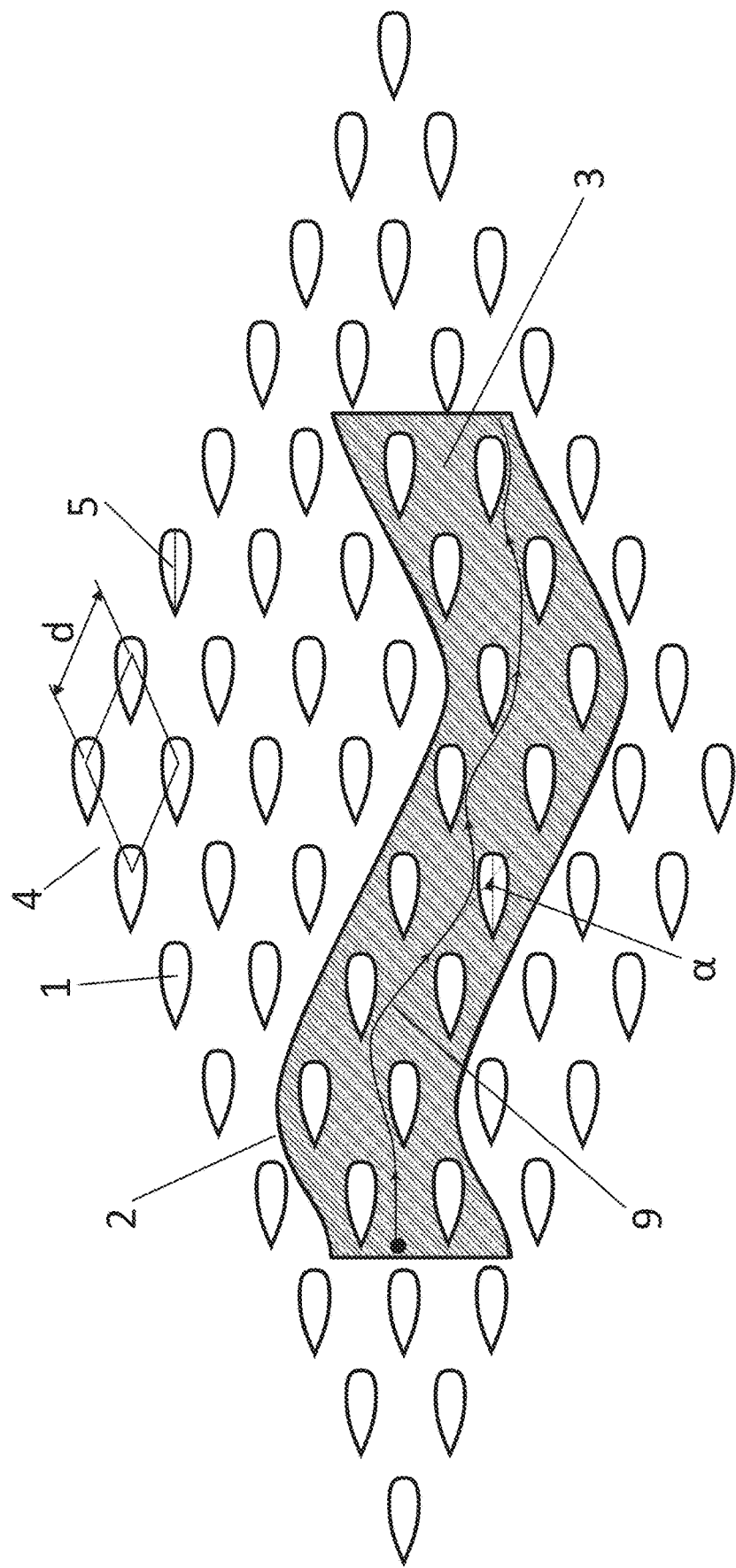
FIG. 1. Depicted is schematic of the meandering microfluidic channel with an array of hydrofoil shaped pillars in an exemplary arrangement.

The components shown in the figures prepared for a better explanation of the microfluidic biological entity separation enhancement device is numbered separately and explanation of each number is given below.

1. Symmetric hydrofoil shaped pillars
2. Meandering microfluidic channel
3. Capture volume
4. Rhombic lattice
5. Chord line
6. Symmetry axis
7. Antibody
8. Target biological entity
9. Streamline carrying target biological entity
10. Straight channel including obstacles
11. Upstream
12. Downstream
13. Ellipse segment
14. Chord
15. Major axis
16. Minor axis
17. Inflow section
18. Outflow section
19. Flow direction
20. Sequence of ellipse segments
21. Preceding ellipse segment
22. Succeeding ellipse segment
23. Straight microchannel
24. Inlet
25. Outlet
d. Side length of a rhombus
α. Attack angle

DETAILED DESCRIPTION OF THE EMBODIMENTS

Figure 2:
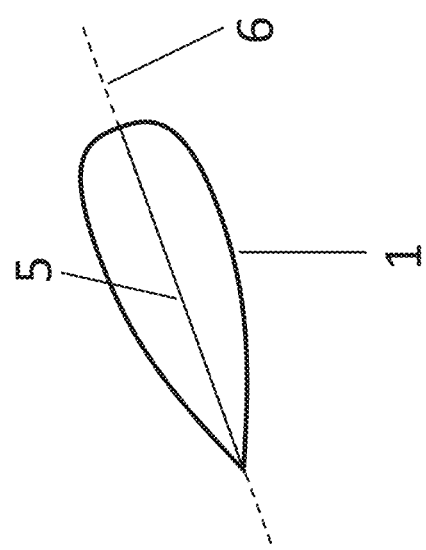
FIG. 2. Depicted is the schematic of a symmetric hydrofoil shaped pillar and its chord line.

The device comprises an array of symmetric hydrofoil shaped pillars (1), a meandering microfluidic channel (2)

including the symmetric hydrofoil shaped pillars (1) acting as obstacles, and a capture volume (3) as shown in FIG. 1. The geometric centers of the symmetric hydrofoil shaped pillars (1) in the array form a rhombic lattice (4). The rhombic lattice (4) is characterized by the side length of a rhombus (d) in the lattice, which is the Euclidean distance between the geometric centers of two neighboring symmetric hydrofoil shaped pillars (1). Another aspect of the array of the symmetric hydrofoil shaped pillars (1) is that the chord lines (5) are parallel to each other. The chord line (5) is defined as a line segment whose endpoints are located on the boundary of the symmetric hydrofoil shaped pillar (1) and is coincident with the symmetry axis (6) of the symmetric hydrofoil shaped pillar (1) (FIG. 2). Boolean subtraction of the array of symmetric hydrofoil shaped pillars (1) from the meandering microfluidic channel (2) defines the capture volume (3) indicated in FIG. 1.

Figure 3:
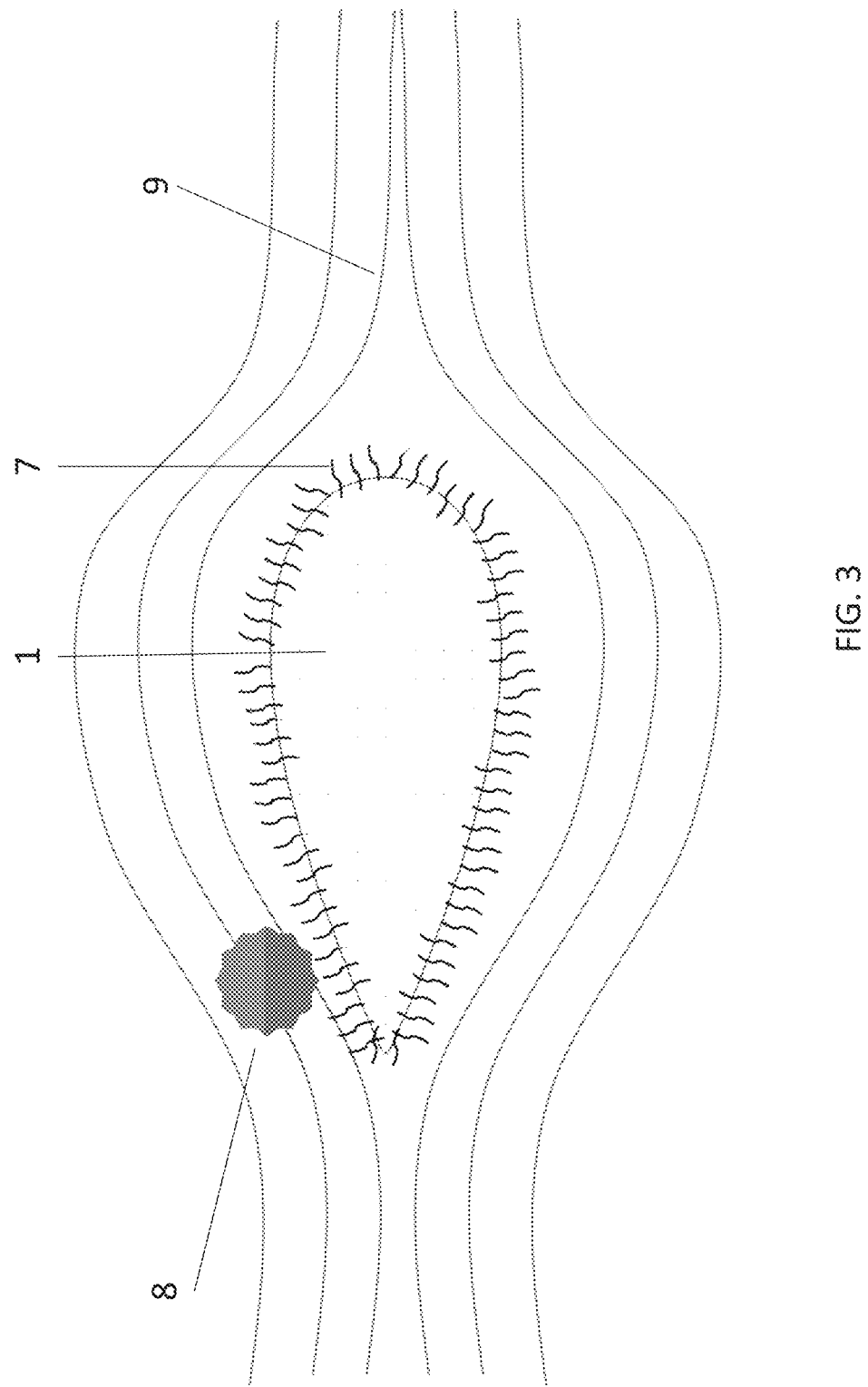
FIG. 3. Depicted is the schematic of interaction between target biological entity and antibodies coated on a single symmetric hydrofoil shaped pillar.

Boundaries of the capture volume (3) including the surface of the symmetric hydrofoil shaped pillars (1) is coated with at least one antibody (7) suitable for the specific capture of the target biological entities (8) according to their distinctive surface proteins among various other entities in a suspension (immunoaffinity-based capture) flowing within the capture volume (3) along the streamlines carrying target biological entities (9) (FIG. 3).

Figure 4:
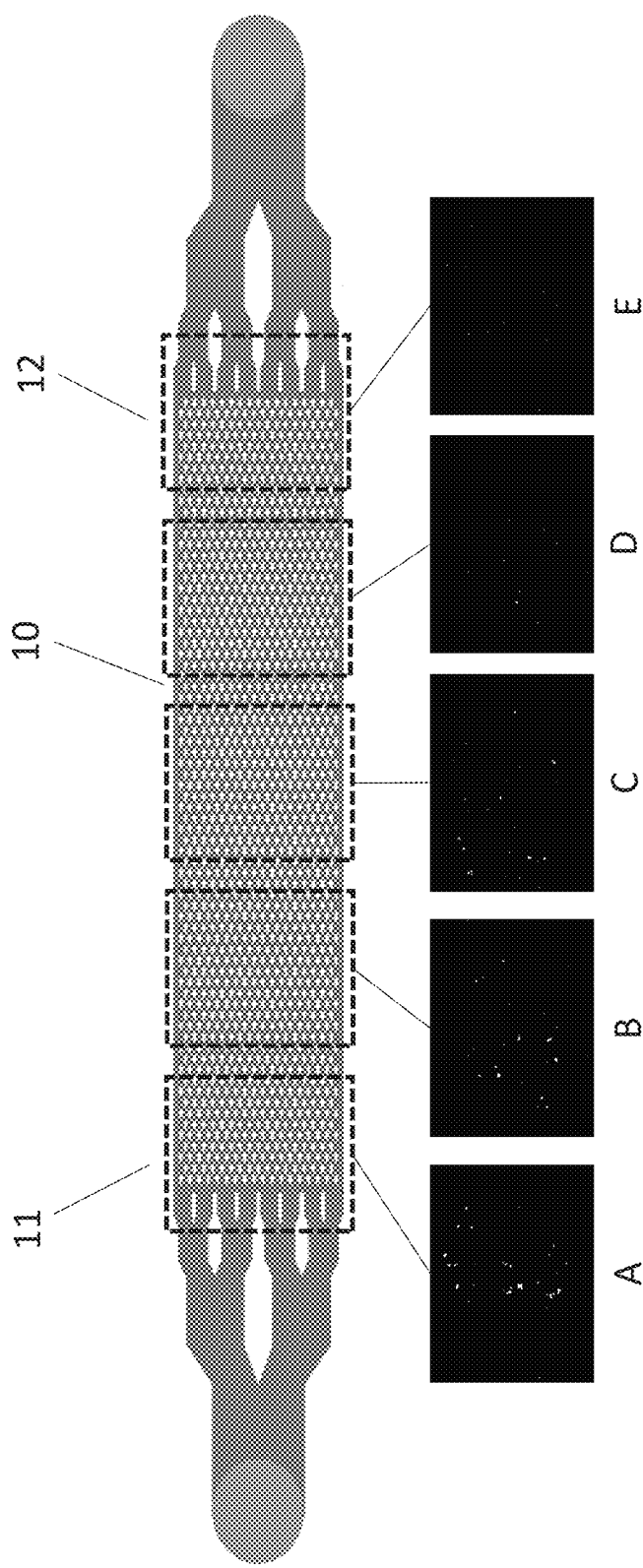
FIG. 4. (A, B, C, D, E) Depicted is the microfluidic device with different capture regions showing the spatial localization of target biological entities captured by specific antibodies in a straight microfluidic channel.

Obstacles are typically used in immunoaffinity-based capture devices in order to increase the surface area, which increases the collision probability of the target biological entities (8) to the antibody (7) coated surface. This increases the entity/surface interaction, thus the capture efficiency of the device. However, in case of a straight channel including obstacles (10), the target biological entity/surface interaction generally takes place at the upstream (11) of the channel and if a target biological entity is not captured at the upstream (11) of the channel, the probability of it being captured at the downstream (12) of the channel drastically decreases (FIG. 4). FIG. 4. A-E show the target biological entities captured at the upstream (11) and downstream (12) of a straight microchannel including obstacles (10). The decrease in the number of captured cells as along this path from upstream to downstream is mainly due to the fact that the fluid flow becomes uniform and the entities follow distinct streamlines which, at low Reynolds number (<<1), do not coincide with the obstacles in the microchannel. In order to keep the entity/surface interaction probability high throughout the whole channel, the chaotic trajectories of the target biological entities (8) should be maintained.

The device of this invention realizes chaotic trajectories of the target biological entities (8) to be maintained throughout the meandering microfluidic channel (2) by continuously altering the attack angles (a), which is the angle between the chord line (5) of the symmetric hydrofoil shaped pillars (1) and the streamlines carrying target biological entities (9) as shown in FIG. 1.

Figure 5:
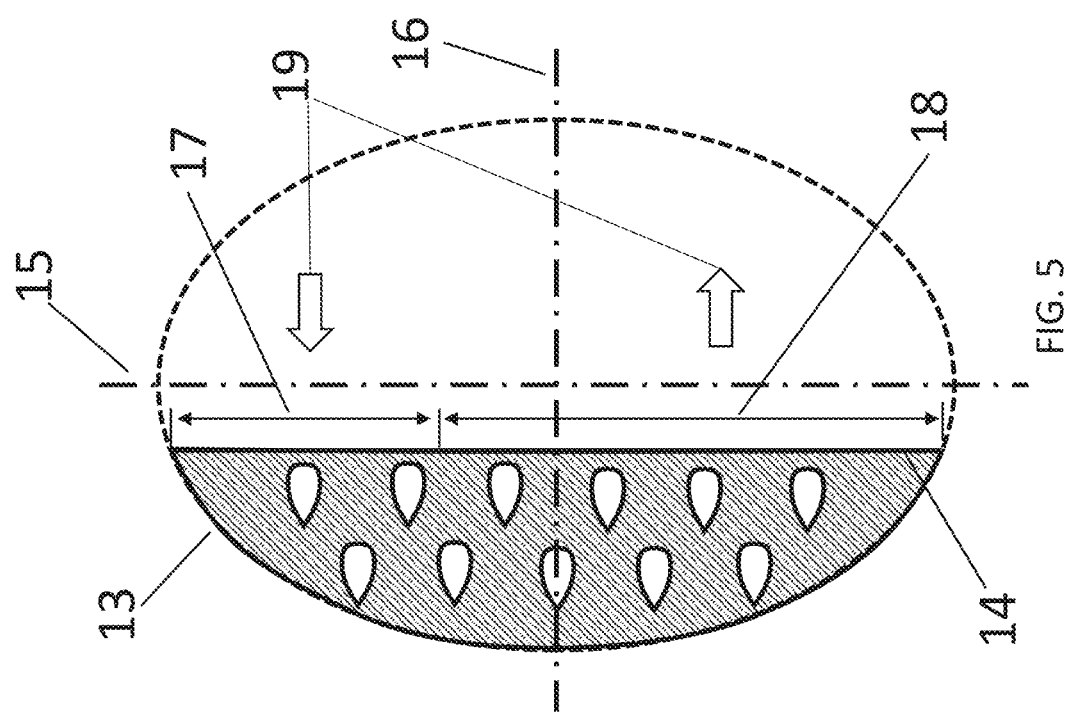
FIG. 5. Depicted is the schematic of an ellipse segment comprising array of symmetric hydrofoil shaped pillars in an exemplary arrangement.

In a particular embodiment of the device, the meandering microfluidic channel (2) comprises an ellipse segment (13), which is characterized by a chord (14) parallel to either of the major axis (15) or the minor axis (16) of the ellipse (FIG. 5). The chord is divided into an inflow section (17) and an outflow section (18), through which target biological entities (8) flow into and out of the ellipse segment (13), respectively as indicated by the flow direction (19).

Figure 6:
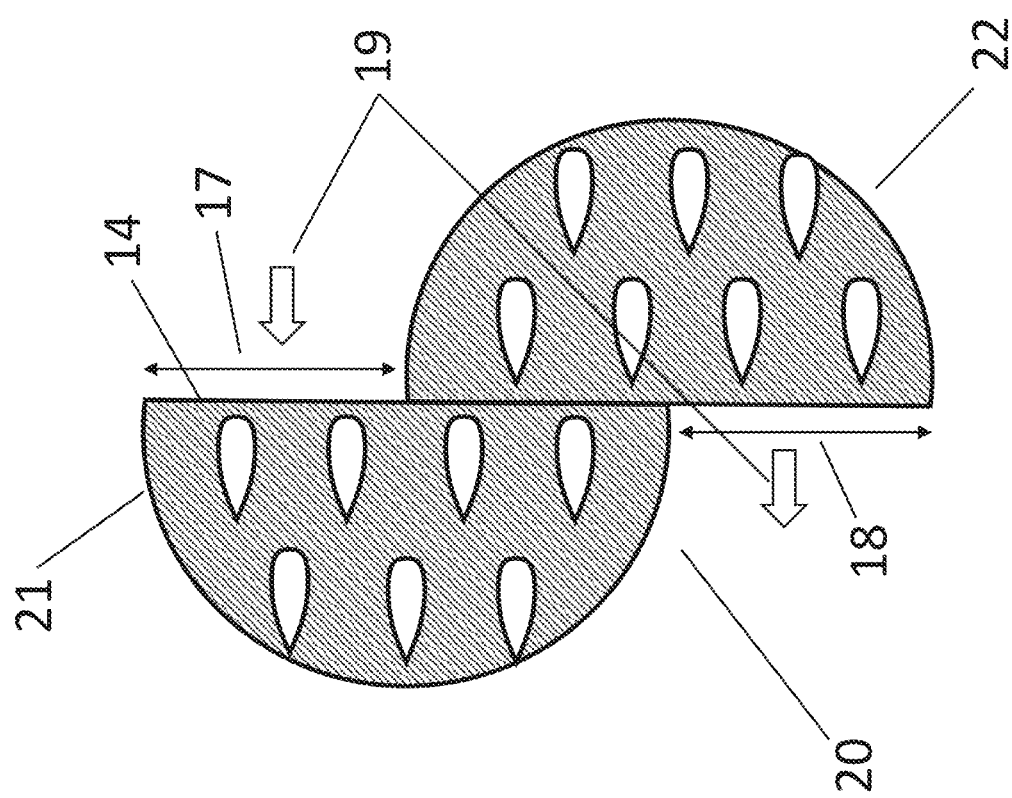
FIG. 6. Depicted is the schematic of sequence of ellipse segments comprising array of symmetric hydrofoil shaped pillars in an exemplary arrangement.
Figure 7:
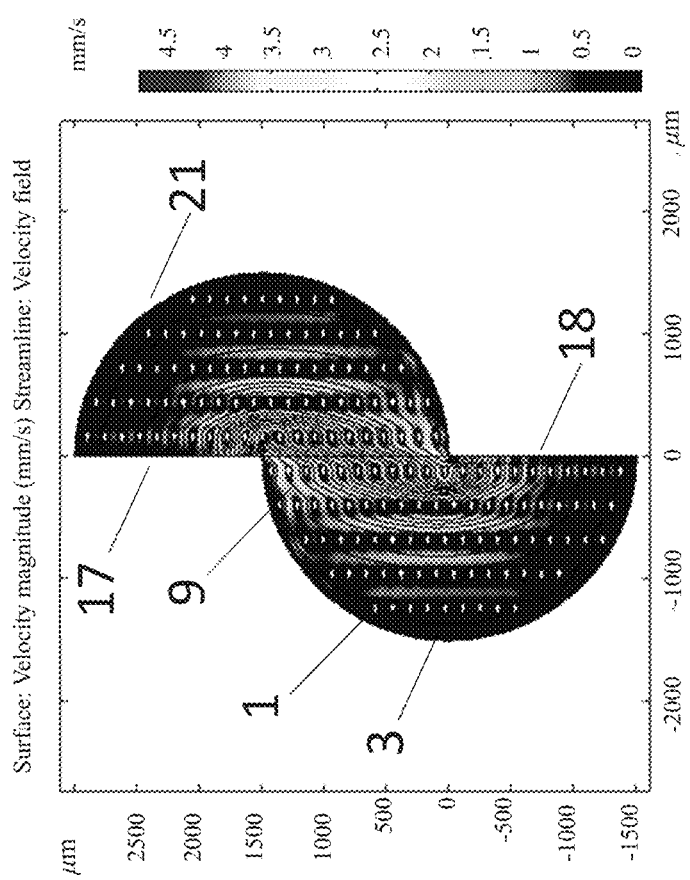
FIG. 7. Depicted is computer simulation of various flow paths of a medium containing target biological entities through an exemplary arrangement of sequence of ellipse segments comprising an array of symmetric hydrofoil shaped pillars.

In another embodiment of the device, the meandering microfluidic channel (2) comprises a sequence of ellipse segments (20) connected to each other (FIG. 6). Sequence of ellipse segments (20) is formed by flipping a preceding ellipse segment (21) in the sequence about its chord (14) and panning by a distance equal to the inflow section (17) along the chord (14) in the direction to the outflow section (18). FIG. 7 shows the results of the computer simulation of the flow inside sequence of two ellipse segments comprising an example array of symmetric hydrofoil shaped pillars (1) depicting the trajectories of streamlines carrying target biological entities (9). Target biological entities (8) enters at the inflow section (17) of the preceding ellipse segment (21) and follows the fluid streamlines which orients the target biological entities (8) towards the boundaries of the capture volume (3). Due to the bending of the flow inside the sequence of ellipse segments, target biological entities (8) collide with the hydrofoil shaped pillars (1) at different attack angles (0°-180°) (FIG. 7).

Figure 8:
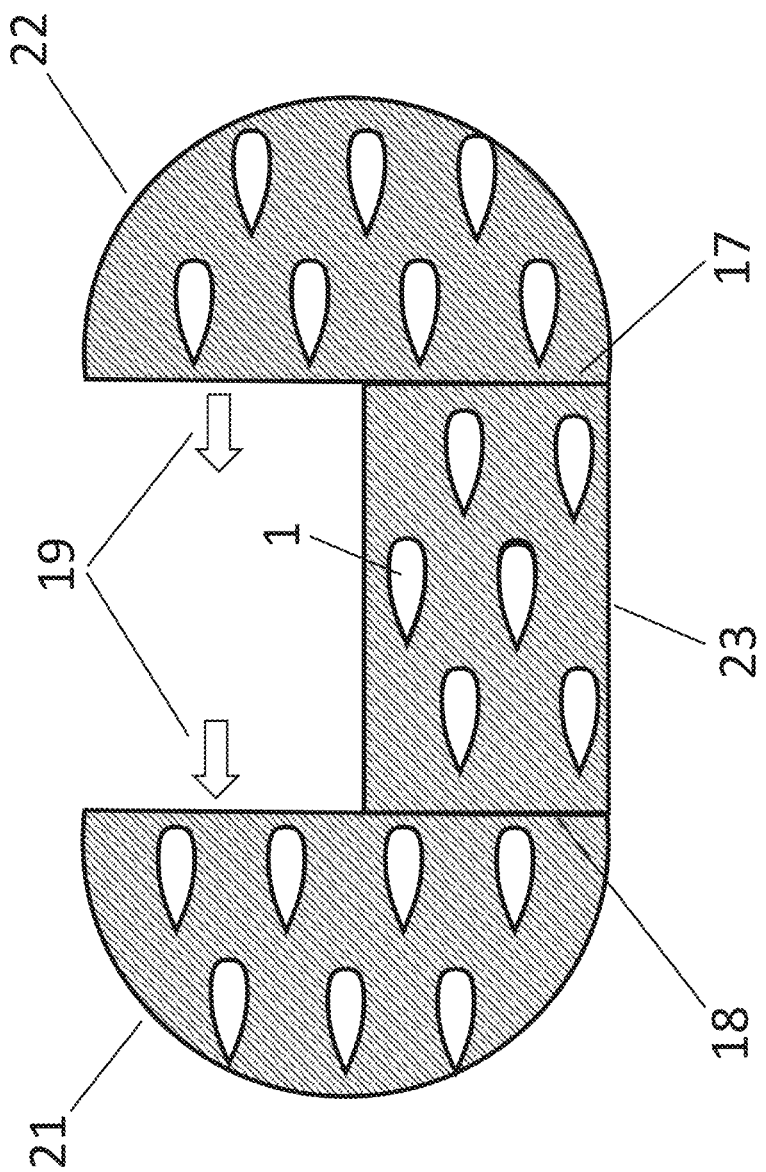
FIG. 8. Depicted is the schematic of two ellipse segments comprising array of symmetric hydrofoil shaped pillars connected through a straight microchannel comprising array of symmetric hydrofoil shaped pillars in an exemplary arrangement.

In another embodiment (FIG. 8), the device comprises at least a channel unit consisting two ellipse segments. Outflow section (18) of the preceding ellipse segment (21) is connected to the inflow section (17) of the succeeding ellipse segment (22) through a straight microchannel (23). The straight microchannel also comprises the array of symmetric hydrofoil shaped pillars (1). Flow direction (19) is indicated in FIG. 8.

Figure 9:
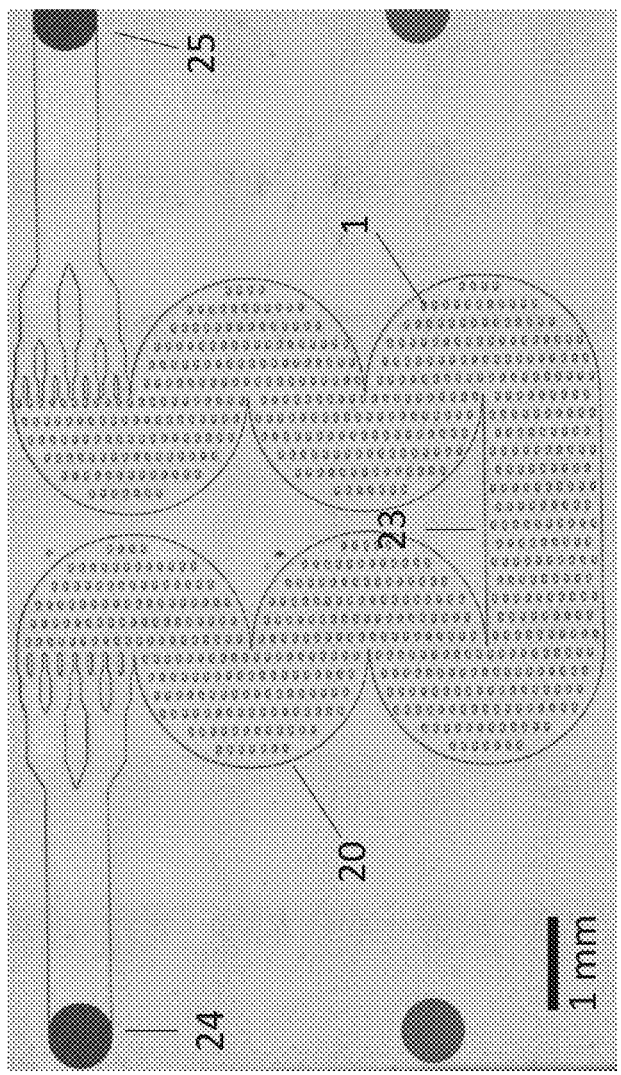
FIG. 9. Depicted is microscope image of an exemplary device formed comprising sequence of ellipse segments and a straight channel comprising array of symmetric hydrofoil shaped pillars.

FIG. 9 shows microscope image of a particular embodiment comprising an inlet (24) for introduction the medium containing target biological entities, an outlet (25), sequence of ellipse segments (20) in the form of half circles, straight microchannel (23), and an array of symmetric hydrofoil shaped pillars (1).

The ellipse segments (13) comprised in the device can be formed by dissecting any ellipse by a chord (14) parallel to either of the major axis (15) or the minor axis (16) of the ellipse as shown in FIG. 5. Therefore, a particular embodiment of the ellipse segment is in the form of a half circle. Additionally, inflow section (17) and outflow section (18) of the chord (14) can be particularly selected to be equal to each other.

The target biological entities (8) captured within the device can be circulating tumor cells, rare cells, peripheral blood cells, or any combination thereof. To prevent clogging and to ensure interaction of the target biological entities (8) with the boundaries of the capture volume (3), the distance between neighboring symmetric hydrofoil shaped pillars (1) can be selected to be three to ten times of the characteristic dimension of the target biological entity (8).

REFERENCES

Harb W., Fan A., Tran T., Danila D. C., Keys D., Schwartz M., Ionescu-Zanetti C., Mutational Analysis of Circulating Tumor Cells Using a Novel Microfluidic Collection Device and qPCR Assay, Translational Oncology Vol. 6, No. 5, 2013.

·Winer-Jones J. P., Vahidi B., Arquilevich N., Fang C., Ferguson S., Harkins D., Hill C., Klem E., Pagano P. C., Peasley C., Romero J., Shartle R., Vasko R. C., Strauss W. M., Dempsey P. W., Circulating Tumor Cells: Clinically Relevant Molecular Access Based on a Novel CTC Flow Cell, PLOS ONE, Vol 9, Issue 1, e86717, 2014.

Martin G., Soper S., Witek M., Yeh J. J., (2016). United States Patent No. U.S. Pat. No. 9,250,242B2.

Zhongliang T., Bhatt R. S., Tsinberg P., (2006). United States Patent No. US 2006/0160243A1.

Skelley A., Smirnov D., Dong Y., Merdek K. D., Sprott K., Carney W., Jiang C., Huang R., Lupascu I., (2014). United States Patent No. US 2014/0154703A1.

Fuchs M., Toner M., (2007). United States Patent No. US 2007/0026417A1.

What is claimed is:

1. A microfluidic device for selective capture of target biological entities, comprising an array of symmetric hydrofoil shaped pillars, wherein geometric centers of the symmetric hydrofoil shaped pillars form a rhombic lattice, a side length of a rhombus in the rhombic lattice, is an Euclidean distance between the geometric centers of two neighboring symmetric hydrofoil shaped pillars, and chord lines of the symmetric hydrofoil shaped pillars are parallel to each other, a meandering microfluidic channel comprising the symmetric hydrofoil shaped pillars acting as obstacles, and a capture volume, wherein the capture volume is defined by a Boolean subtraction of the array of the symmetric hydrofoil shaped pillars from the meandering microfluidic channel, wherein the surface of the symmetric hydrofoil shaped pillars of the capture volume is coated with at least one antibody, said at least one antibody configured for the specific capture of the target biological entities.

2. The microfluidic device according to claim 1, wherein the meandering microfluidic channel comprises an ellipse segment comprising a chord parallel to a major or minor axis of an ellipse, wherein the chord is divided into an inflow section and an outflow section, wherein a target biological entity flow into and out of the ellipse segment through the inflow section and the outflow section, respectively.

3. The microfluidic device according to claim 2, wherein a length of the inflow section is equal to a length of the outflow section.

4. The microfluidic device according to claim 2, wherein the meandering microfluidic channel comprises a sequence of ellipse segments connected to each other, wherein a succeeding ellipse segment is formed by flipping a preceding ellipse segment about a chord of the preceding ellipse segment and panned by a distance equal to the inflow section along the chord.

5. The microfluidic device according to claim 4, comprising at least a channel unit, wherein the channel unit consists of two ellipse segments, wherein the outflow section of the preceding ellipse segment is connected to the inflow section of the succeeding ellipse segment through a straight microchannel, wherein the straight microchannel comprises the array of symmetric hydrofoil shaped pillars.

6. The microfluidic device according to claim 2, wherein the ellipse segment is in a form of a half-circle.

7. The microfluidic device according to claim 1, wherein a distance between neighboring symmetric hydrofoil shaped pillars is three to ten times of a characteristic dimension of a target biological entity.

8. The microfluidic device according to claim 7, wherein the target biological entity is selected from group consisting of Circulating Tumor Cells (CTC), rare cells, peripheral blood cells, or any combination of the CTC, the rare cells or the peripheral blood cells.

9. The microfluidic device according to claim 3, wherein the meandering microfluidic channel comprises a sequence of ellipse segments connected to each other, wherein a succeeding ellipse segment is formed by flipping a preceding ellipse segment about a chord of the preceding ellipse segment and panned by a distance equal to the inflow section along the chord.

10. The microfluidic device according to claim 2, wherein a distance between neighboring symmetric hydrofoil shaped pillars is three to ten times of a characteristic dimension of a target biological entity.

11. The microfluidic device according to claim 3, wherein a distance between neighboring symmetric hydrofoil shaped pillars is three to ten times of a characteristic dimension of a target biological entity.

12. The microfluidic device according to claim 4, wherein a distance between neighboring symmetric hydrofoil shaped pillars is three to ten times of a characteristic dimension of a target biological entity.

13. The microfluidic device according to claim 5, wherein a distance between neighboring symmetric hydrofoil shaped pillars is three to ten times of a characteristic dimension of a target biological entity.

14. The microfluidic device according to claim 6, wherein a distance between neighboring symmetric hydrofoil shaped pillars is three to ten times of a characteristic dimension of a target biological entity.

* * * * *